United States Patent
Lee et al.

(10) Patent No.: US 11,420,191 B2
(45) Date of Patent: Aug. 23, 2022

(54) SHAPED DEHYDROGENATION CATALYSTS AND PROCESS FOR CONVERTING PARAFFINS TO CORRESPONDING OLEFINS, USING SAME

(71) Applicants: SK Innovation Co., Ltd., Seoul (KR); SK Global Chemical Co., Ltd., Seoul (KR)

(72) Inventors: Ho Won Lee, Daejeon (KR); Ju Hwan Im, Daejeon (KR); Hee Soo Kim, Daejeon (KR); Hye Jin Park, Daejeon (KR); Je Mi Lim, Daejeon (KR); Dae Hyun Choo, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 0 days.

(21) Appl. No.: 16/951,233

(22) Filed: Nov. 18, 2020

(65) Prior Publication Data

US 2021/0170370 A1 Jun. 10, 2021

(30) Foreign Application Priority Data

Nov. 20, 2019 (KR) .................... 10-2019-0149580

(51) Int. Cl.
| | | |
|---|---|---|
| *B01J 21/08* | (2006.01) | |
| *B01J 23/75* | (2006.01) | |
| *B01J 35/02* | (2006.01) | |
| *C07C 5/333* | (2006.01) | |
| *B01J 37/08* | (2006.01) | |

(52) U.S. Cl.
CPC .............. *B01J 23/75* (2013.01); *B01J 21/08* (2013.01); *B01J 35/026* (2013.01); *B01J 37/08* (2013.01); *C07C 5/3332* (2013.01); *C07C 2521/08* (2013.01); *C07C 2523/75* (2013.01)

(58) Field of Classification Search
CPC ... B01J 21/08; B01J 23/75; B01J 23/78; B01J 35/002; B01J 35/026; B01J 37/08; B01J 37/0201; B01J 37/06; B01J 37/0009; B01J 37/0207; C07C 5/3332; C07C 5/3335; C07C 2521/08; C07C 2523/75; C07C 2523/78; C07C 11/06; Y02P 20/52
USPC ....... 502/232, 240, 250, 251, 252, 254, 258, 502/260
See application file for complete search history.

(56) References Cited

U.S. PATENT DOCUMENTS

| | | | |
|---|---|---|---|
| 9,192,919 B2 * | 11/2015 | Hock | ............. B01J 37/0209 |
| 2016/0074838 A1 * | 3/2016 | Hock | ............. B01J 37/0203 |
| | | | 502/259 |

FOREIGN PATENT DOCUMENTS

EP        3928864        * 12/2021

OTHER PUBLICATIONS

Jimenez et al., "Influence of coordination environment of anchored single-site cobalt catalyst on CO2 hydrogenation", Wiley Online Library, 2019, pp. 1-10.*
Goldsmith et al., "Beyond Ordered Materials: Understanding Catalytic Sites on Amorphous Solids", ACS Catal., 2017, 7, pp. 7543-7557.*
Schweitzer et al., "Propylene Hydrogenation and Propane Dehydrogenation by a Single-Site Zn2+ on Silica Catalyst", ACS Catalysis, 2014, pp. 1091-1098, American Chemical Society.

* cited by examiner

*Primary Examiner* — Elizabeth D Wood
(74) *Attorney, Agent, or Firm* — The Webb Law Firm

(57) ABSTRACT

Disclosed herein are a dehydrogenation catalyst having single-atom cobalt loaded on a silica-based, shaped support, a preparation method therefor, and a method for preparing an olefin by dehydrogenating a corresponding paraffin, particularly light paraffin in the presence of the dehydrogenation catalyst.

17 Claims, 3 Drawing Sheets

SHAPED DEHYDROGENATION CATALYSTS AND PROCESS FOR CONVERTING PARAFFINS TO CORRESPONDING OLEFINS, USING SAME

CROSS-REFERENCE TO RELATED APPLICATION

This application claims priority to Korean Patent Application No. 10-2019-0149580 filed Nov. 20, 2019, the disclosure of which is hereby incorporated by reference in its entirety.

BACKGROUND OF THE INVENTION

1. Field of the Invention

The present disclosure relates to shaped dehydrogenation catalysts and a process for converting paraffins to olefins, using the same. More particularly, the present disclosure relates to a dehydrogenation catalyst having single-atom cobalt loaded onto a silica-based molded support, a preparation method therefor, and a method for producing olefins by dehydrogenating corresponding paraffins, particularly light paraffins in the presence of the dehydrogenation catalyst.

2. Description of the Prior Art

Light olefins, such as ethylene, propylene, butylene, so on, are main chemical raw materials used as building blocks for chemical products (oxo-alcohols, acrylonitrile, propylene oxide, butanol, acrylic acid, etc.) and plastic products (polypropylene, ethylene-propylene rubber, etc.), finding a broad range of applications in the petrochemical industry. Inter alia, propylene, which is a colorless compound of low boiling point, is traded typically at a polymer grade (at least about 99.5% purity), chemical grade (about 90-96% purity), and refinery grade (about 50-70% purity).

Generally, light olefins are produced by thermal cracking of naphtha or kerosene under supply of steam (that is, steam cracking). However, with the growth of demand on light olefins, thermal cracking-type methods have difficulty in meeting the growing demand. In response to the demand, various synthesis methods (for example, catalytic cracking processes of light fractions, etc.) have been proposed. The products obtained by the steam cracking, catalytic cracking, etc. are typically a mixture of various hydrocarbons including methane, ethane, propane, and C5/C6+ paraffinic hydrocarbons as well as olefins (ethylene, propylene, etc.).

The composition of mixed hydrocarbons can be adjusted by modifying operation conditions of the processes. However, such modification cannot be a sufficient strategy when a market demand is higher for a specific product than other co-products. For example, market demands particularly for propylene in many regions are rapidly growing than for ethylene. Such low olefin yields from which conventional commercial processes suffer require catalyst reaction technologies for increasing selectivity for olefins as much as possible.

Examples of commercial dehydrogenation techniques in current use are summarized in Table 1, below.

TABLE 1

|  | CATOFIN | Oleflex | Uhde | SABIC |
| --- | --- | --- | --- | --- |
| Manufacturer | Lummus | UOP | Lrupp-Uhde | SABIC |
| Reactor | Adiabatic fixed bed | Adiabatic moving bed | DH + ODH- Adiabatic | Adiabatic fixed bed and FBR |
| Operation type | Cyclic | Continuous | Cyclic | Cyclic |
| Feedstock | C3-C4 | C3-C4 | C3-C4 | C3 |
| Catalyst | Cr-based loaded catalyst | Pt-Sn- based loaded catalyst | Pt-Sn- based loaded catalyst | Pt-Sn- based loaded catalyst |
| Rxn. Temp. (° C.) | 565-649 | 550-620 | DH: 550-590 ODH: about 600 | 560-600 |
| Rxn. Press. (bar) | 03-0.5 | 2-3 | 5-6 | 0.1-6 |
| Cycle time | 15-30 min. | — | 8 hrs | 15-30 min. |

For the commercial processes exemplified above, a feedstock in a mixed gas form is supplied while chromium- or platinum-based (e.g., Pt—Sn) catalysts are mainly employed. Iron oxide-based catalysts and gallium/zeolite catalysts are also known to be applicable to the dehydrogenation of paraffins. In addition, although generally undergoing a regeneration process after being inactivated with the generation of coke during reactions, dehydrogenation catalysts are required to maintain catalytic activity during multiple cycles of regeneration.

In recent years, there has been a growing interest in catalyst technology for utilizing all metal elements supported on a support. Conventional metal-supported catalysts have catalytic metal particles assembled on the supports. Given a broad size distribution and irregular morphologies, the assembled metal particles cannot take full advantage of metal active sites and thus have undesirable influence on catalyst activity or selectivity. In contrast, single-atom catalysts provide the advantage that catalyst activity can be maximized by downsizing metal nanostructures to metal active sites distributed to an atomic level.

In this regard, there is a technique known to convert propane to propylene through dehydrogenation in the presence of a catalyst having a single-atom type active metal (e.g., zinc) supported onto a support such as silica (e.g., ACS Catal. 2014, 4, 4, 1091-1098). In this document, a mixed gas containing 3% of propane and the balance of argon (Ar), which is an inert gas, is used as a reactant with the aim of selectively converting paraffins to the corresponding olefins while suppressing the formation of by-products. However, a feedstock containing a low content of paraffins is improper from the viewpoint of commerce. Furthermore, the catalyst may be thermally unstable in a high temperature reaction of about 500 to 600° C. and in a dehydrogenation processes that proceed in high temperature and regeneration conditions because the catalyst is thermally treated at as low as of 300° C.

There is therefore a need for a better catalytic activity that is highly stable and shows maximum advantage of single-atom catalysts. Particularly, single-atom catalysts have been difficult to commercialize because shaped catalysts do not guarantee single atom characteristics.

SUMMARY OF THE INVENTION

An embodiment according to the present disclosure provides a single-atom cobalt (Co) loaded dehydrogenation catalyst that not only exhibits excellent catalytic stability, but also is made of a molded body suitable for commercialization, and a preparation method therefor.

An embodiment according to the present disclosure provides a dehydrogenation process which can attain higher conversion of paraffins even for a feedstock containing a high concentration of paraffins and excellent selectivity for corresponding olefins.

Provided according to a first aspect of the present disclosure is a method for preparation of a cobalt-based, shaped single-atom catalyst, the method comprising the steps of:

combining a silica binder and a silica powder for support material in an aqueous medium to prepare a molding paste;

molding the paste into a silica-based, molded support;

contacting the silica-based, molded support with an alkali metal salt in an aqueous medium to form an alkali metal-treated, silica-based, molded support, before or after which pH adjustment is made with a base, wherein at least a part of the alkali metal ions are electrostatically adsorbed on the surface of the silica-based, molded support;

contacting the alkali metal-treated, silica-based, molded support with an aqueous solution of a first cobalt precursor to form a first cobalt- and alkali metal-containing, silica-based, molded support, the aqueous solution of the first cobalt precursor being adjusted in pH by adding a base thereto, with the first cobalt precursor having an oxidation number of 3+, wherein at least a part of the cobalt ions having an oxidation number of 3+ is electrostatically adsorbed on the alkali metal-treated, silica-based, molded support; and thermally treating the first cobalt- and alkali metal-containing silica-based, molded support, whereby the cobalt having an oxidation number of 2+ and the alkali metal having an oxidation number of 1+, respectively, exist in an isolated form of single-atom on the silica-based, molded support while the cobalt having an oxidation number of 2+ is tetrahedrally coordinated at the three-membered siloxane ring present on the surface of the silica-based, molded support.

According an exemplary embodiment, the method may further comprise the steps of: contacting the first cobalt- and alkali metal-containing silica-based, molded support with an aqueous solution of a second cobalt precursor having an oxidation number of 3+ to form a second cobalt- and alkali metal-containing silica-based, molded support, the aqueous solution of the second cobalt precursor being adjusted in pH by addition of a base thereto; and thermally treating the second cobalt- and alkali metal-containing silica-based, molded support.

Provided according to a second aspect of the present disclosure is a method for preparation of a cobalt-based, shaped single-atom catalyst, the method comprising the steps of:

combining a silica binder and a silica powder support material in an aqueous medium to prepare a molding paste;

molding the paste into a silica-based, molded support;

contacting the silica-based, molded support with an alkali metal salt in an aqueous medium to form an alkali metal-treated, silica-based, molded support, before or after which pH adjustment is made with a base, wherein at least a part of the alkali metal ions are electrostatically adsorbed on the surface of the silica-based, molded support;

contacting the alkali metal-treated, silica-based, molded support with an aqueous solution of a first cobalt precursor to form a first cobalt- and alkali metal-containing, silica-based, molded support, the aqueous solution of the first cobalt precursor being adjusted in pH by adding a base thereto, with the first cobalt precursor having an oxidation number of 3+, wherein at least a part of the cobalt ions having an oxidation number of 3+ is electrostatically adsorbed on the alkali metal-treated, silica-based, molded support;

contacting the first cobalt- and alkali metal-containing, silica-based, molded support with an aqueous solution of a second cobalt precursor to form a second cobalt- and alkali metal-containing, silica-based, molded support, the aqueous solution of the second cobalt precursor being adjusted in pH by adding a base thereto, with the second cobalt precursor having an oxidation number of 3+;

thermally treating the second cobalt- and alkali metal-containing silica-based, molded support, whereby the cobalt having an oxidation number of 2+ and the alkali metal having an oxidation number of 1+, respectively, exist in an isolated form of single-atom on the silica-based, molded support while the cobalt having an oxidation number of 2+ is tetrahedrally coordinated at the three-membered siloxane ring present on the surface of the silica-based, molded support.

Provided according to a third aspect of the present disclosure is a dehydrogenation catalyst, comprising:

a silica-based, molded support having an alkali metal adsorbed thereon; and cobalt, as an active metal, loaded to the silica-based, molded support, wherein the dehydrogenation catalyst is a cobalt-based, molded single-atom catalyst in which the cobalt having an oxidation number of 2+ and the alkali metal having an oxidation number of 1+, respectively, exist in an isolated form of single-atom on the silica-based, molded support while the cobalt having an oxidation number of 2+ is tetrahedrally coordinated at the three-membered siloxane ring present on the surface of the silica-based, molded support.

Provided according to a fourth aspect of the present disclosure is a method for production of an olefin, the method comprising the steps of:

providing a feedstock containing a light paraffin;

subjecting the feedstock to dehydrogenation at a temperature of 500 to 700° C. under a pressure of 0.3 to 2 bar in presence of the catalyst described above; and recovering the olefin corresponding to the light paraffin from the dehydrogenation product.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Figure 1:
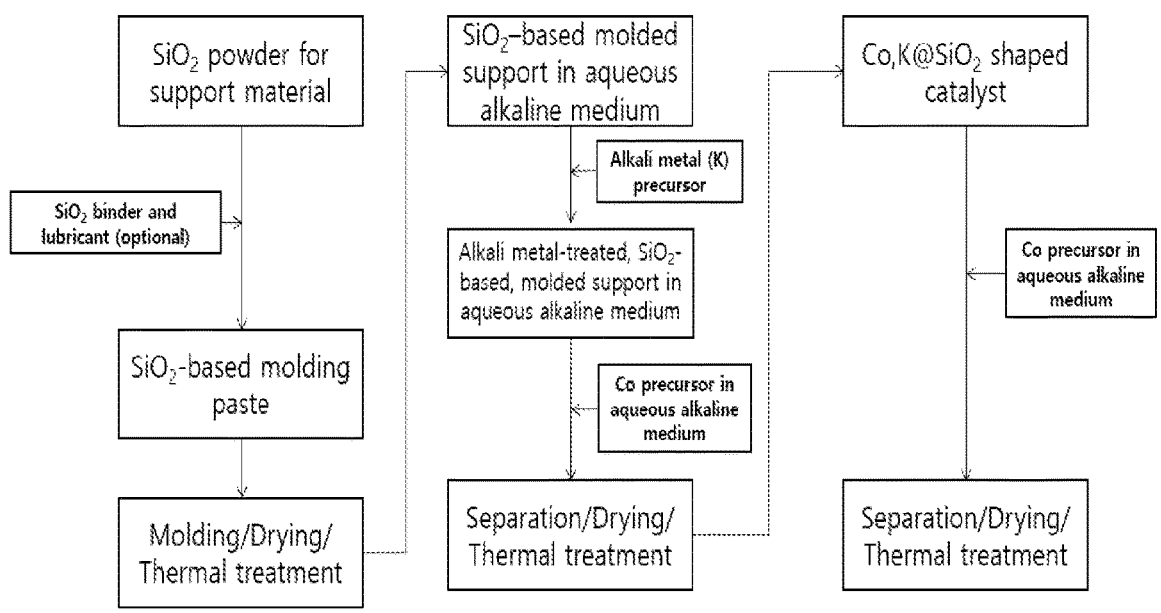
FIG. 1 is a schematic view illustrating a series of processes for preparing a silica-based, molded support and a single-atom catalyst having cobalt loaded to the support according to an exemplary embodiment.

The present disclosure can be all accomplished by the following description. It is to be understood that the following description illustrates preferable embodiments of the present disclosure, but the present disclosure is not necessarily limited thereto. It is also to be understood that the accompanying drawings are included to provide a further understanding of the present disclosure and are not intended to limit the scope of the present disclosure.

The terms used herein are defined as follows.

The term "heterogeneous catalyst" refers to a catalyst that is present in a different phase from a reactant in a catalyst reaction process. For example, a heterogeneous catalyst may remain undissolved in a reaction medium. When a heterogeneous catalyst is given, the onset of a reaction occurs with the diffusion and adsorption of reactants onto the surface of the heterogeneous catalyst. After completion of the reaction, a product needs to be desorbed from the surface of the heterogeneous catalyst.

The term "support", as used herein, refers to a material (typically a solid-phase material) with a high specific surface area, to which a catalytically active component is attached, and the support may or may not be involved in a catalytic reaction.

As used herein, the term "crystalline" refers typically to any solid substance in which atoms are arranged to have a lattice structure (e.g., a three-dimensional order) while the term "amorphous" refers to any solid substance that does not have such a lattice structure. The substances may each be identified by X-ray diffraction (XRD), nuclear magnetic resonance (NMR), differential scanning calorimetry (DSC), or a combination thereof.

As used herein, the term "light paraffin" refers to a paraffin of 2 to 5 carbon atoms, more particularly, a paraffin of 3 or 4 carbon atoms, as exemplified by ethane, propane, n-butane, and pentane. In addition, "corresponding olefin" refers to an olefin resulting from the removal of a hydrogen molecule from a light paraffin in a feedstock by dehydrogenation and thus having the same number of carbon atoms as the paraffin.

The term "silica", as used herein, refers to a substance of tetrahedral coordination in which four oxygen atoms bind to one silicon atom.

As used herein, the term "porous silica" refers to a three-dimensional network silica having porosity, which may be composed of an aggregate of primary silica particles.

As used herein, the term "single-atom catalyst" refers generally to a catalytic material in which an active component for a specific catalysis reaction is dispersed in the form of single atoms in any framework or support such as a metal oxide surface. Typically, a single-atom catalyst can be characterized using any analysis apparatuses having atomic level resolution, such as HAADF-STEM (high-angle annular dark-field scanning transmission electron microscopy).

Cobalt-Based, Shaped Single-Atom Catalyst

Provided according to an embodiment of the present disclosure is a cobalt-based, shaped single-atom catalyst that is suitable not only for converting a feedstock containing a high concentration of paraffins (Particularly, light paraffins) to corresponding olefins with high conversion and selectivity, but also exhibits notable thermal stability even upon exposure to high temperatures during dehydrogenation and finds suitable applications in commercial processes.

According to an embodiment, the catalyst may be a heterogeneous catalyst in which a single site (atom) cobalt as an active metal is supported (or immobilized) onto a silica-based, molded support having an alkali metal immobilized (adsorbed) in a form of single atom thereon (that is, treated with an alkali metal). In this regard, the silica-based, molded support according to an exemplary embodiment may comprise a combination of a silica powder (e.g., wet (hydrated) silica) for a support and a silica binder (e.g., colloidal silica).

In the silica-based, molded support having an alkaline metal adsorbed thereto, the alkali metal (or alkali metal ion) positively charged on a silica and having an oxidation number of 1+ is bound in an isolated form of single atom with negatively charged $SiO^-$ on the surface of the silica-based molded support through electrostatic interaction (or adsorption). In addition, cobalt (Co (II)) or cobalt ions with an oxidation number of 2+ exist as in an isolated form of single atom on the surface of the silica-based, molded support. The cobalt in a single-atom form is tetrahedrally coordinated at the three-membered siloxane ring present on the surface of the silica-based, molded support.

As such, an alkali metal in a form of single atom is introduced to a silica-based, molded support, prior to supporting (or loading) cobalt onto the support, to define the sites available for supporting cobalt, whereby the alkali metal is interposed between cobalt atoms to effectively restrain the aggregation caused by polygomerization, such as dimerization between cobalt atoms.

In addition, with the introduction of an alkali metal thereto, the catalyst according to the present embodiment exhibits an increased resistance against the reduction of the cobalt in an oxidation state to an elemental state by hydrogen generated upon the dehydrogenation and thus advantageously resists a sharp decrease in activity during the reaction. In this regard, the function resulting from the introduction of the alkali metal to a shaped catalyst is conceptually distinguished from the use of an alkali metal as a promoter in the conventional catalysts to provide the functions of controlling strong acid sites present in the supports rather than central metal ingredients, suppressing strong acid site-induced dissociation of carbon-carbon bonds in paraffins or coke formation to increase the selectivity of the catalytic reaction, and preventing the catalyst deactivation caused by coke.

In the present embodiment, the introduction of an alkali metal aims to control the deposition (e.g., impregnation) site and/or amount of cobalt as the central metal, which is locally concentrated and is thus liable to aggregate, but not to function as a promoter as in the conventional dehydrogenation catalysts. Theoretically, thus, the alkali metal may interfere with the catalytic reactions. In the embodiment, however, the introduction of an alkali metal is considered to provide the advantage of increasing the stability of the catalyst by ultimately suppressing the reduction and/or aggregation of the cobalt metal while minimizing those disadvantages. In detail, cobalt supported in a single atom form without treatment with an alkali metal undergoes Co—O—Co dimer formation and aggregation during the dehydrogenation reaction. Particularly, when the catalyst is exposed to high temperatures with the progression of the reaction or when dehydrogenation is conducted using a feedstock containing a high concentration of paraffins, the aforementioned problems notably arise, decreasing the catalytic activity.

According to an exemplary embodiment, the alkali metal may be at least one selected from the group consisting of sodium (Na), potassium (K), and cesium (Cs). More specifically, the alkali metal may be potassium (K) because potassium has an ion size which enables it to be located around cobalt bound to the 3-membered siloxane ring such that effective stabilization might be realized in cooperation with cobalt.

In this regard, a content of the alkali metal in the catalyst may range, for example, from about 0.00001 to 1% by weight, particularly from about 0.005 to 1% by weight, and more particularly, from about 0.01 to 0.5% by weight. According to an exemplary embodiment, the dehydrogenation catalyst in a shaped form contains cobalt at a content (loading amount) of, for example, from about 0.5 to 5% by weight, particularly from about 0.7 to 3% by weight, and more particularly from about 1 to 2.5% by weight. The loading amount may slightly vary depending on properties of the silica-based, molded support, etc., but may be controlled taking into account the maximum amount of the cobalt existing in a single atom, typically about 2 to 3% by weight.

In an exemplary embodiment, the weight ratio of cobalt (Co)/alkali metal in the catalyst may range, for example, from about 1 to 1000, particularly from about 10 to 800, more particularly from about 50 to 600, and most particularly from about 100 to 500. An excessive loading amount of cobalt relative to the alkali metal accounts for the presence of redundant cobalt ions within a locally restricted area. In this circumstance, deficiency of the alkali metal component could cause the reduction or aggregation of cobalt ions on the surface of catalyst, resulting in the deactivation of the cobalt single-atom catalyst. On the other hand, when the relative loading amount of cobalt to the alkali metal is too small, the alkali metal occupies relatively much space to act as a barrier against the access of the reactant light paraffin to the catalyst, greatly reducing the conversion. In consideration of this, the weight ratio of cobalt (Co)/alkali metal may be advantageously adjusted within the range.

So long as the cobalt-based, shaped catalyst is applicable to commercial processes, the catalyst is not limited to particular shapes and/or dimensions (or sizes). In an exemplary embodiment, the catalyst may be a cylinder, a granule, a pellet, a tablet, a sphere, or a trilobe in shape. In this regard, a cylindrical catalyst may range in diameter, for example, from about 0.1 to 5 mm (particularly about 0.5 to 4 mm, and more particularly about 1 to 3 mm), with a length of, for example, about 0.5 to 20 mm (particularly about 1 to 15 mm, and more particularly about 3 to 10 mm). In addition, when the catalyst has the shape of a granule, a pellet, a tablet, or a sphere, its average size may be, for example, about 0.1 to 10 mm (particularly about 0.5 to 7 mm, and more particularly about 1 to 5 mm).

In order to reduce the pressure drop at front and rear ends, which is one of the important process variables in commercial processes (especially for production of propylene) where high-temperature reaction and frequent gas replacement occur, the catalyst may advantageously have uniform shapes with sufficient pores therein when loaded into the reactor, as described above.

Method for Preparing Cobalt-Based, Shaped Single-Atom Catalyst

A series of processes in which a silica-based molded support is prepared and cobalt is supported or loaded onto the support to prepare a single-atom catalyst in accordance with an embodiment of the present disclosure is depicted in FIG. 1. The depicted embodiment is given only for an illustrative purpose, but not to limit the present disclosure.

Preparation of Silica-Based, Molded Support

According to an exemplary embodiment, a silica binder and a silica powder for support material are combined with each other to form a molding paste.

The silica powder, which is one of the main components for the molding paste, is not limited to particular types, but may advantageously employ high-purity silica that is as low in impurity content as possible. According to an exemplary embodiment, the silica may be amorphous silica, particularly porous amorphous silica, for example, wet (hydrated) silica (silica gel and precipitated silica). The lower is the crystallinity, the more advantageous the catalyst is. Given as a fine powder, the silica has a large amount of silanol groups and siloxane groups present on the molecule surface thereof. The silanol (hydroxyl) groups on the silica surface may exist in the three types: isolated (Si—OH), vicinal (linked through a hydrogen bond), and germinal (HO—Si—OH), or may be rich in the local combination composed of 2:1 of isolated: vicinal type. Meanwhile, when amorphous dry silica (fumed silica, pyrogenic silica) is incorporated at more than a particular level (for example, in an amount of about 20% by weight or more of the silica powder for support material), the supported single-atom cobalt may become poor in stability upon exposure to a high temperature at which dehydrogenation occurs (for example, cobalt grows in an oxide form to facilitate coke formation).

According to a particular embodiment, the silica has a specific surface area (e.g., BET specific area) of, for example, at least about 100 $m^2/g$, particularly about 200 to 1500 $m^2/g$, and more particularly about 300 to 1000 $m^2/g$. The silica may range in pore volume, for example, from about 0.1 to 10 $cm^3/g$, particularly from about 0.3 to 5 $cm^3/g$, and more particularly from about 0.5 to 3 $cm^3/g$ and in pore size (average diameter), for example, from about 0.5 to 200 nm, particularly from about 1 to 100 nm, and more particularly from about 3 to 30 nm. It, however, should be understood that the numerical ranges are given for an illustrative purpose.

In the meantime, the silica binder available for preparing the molding paste can bind the silica for support material. In addition, the silica molded support prepared using the silica binder should allow cobalt as the central metal to be maintained stably in a form of single-atom.

According to an exemplary embodiment, the silica binder may be colloidal silica. The term "colloidal silica" refers to a suspension of silica particles. Colloidal silica may be prepared typically through wet chemical synthesis (particularly, hydrolyzing organic silicate in an organic solvent such as alcohol). The colloidal silica may have a particle size of, for example, about 10 to 1000 Å, particularly about 100 to 500 Å. In addition, the silica binder may be, for example, at least about 95%, particularly at least about 99%, and more particularly at least about 99.9% in purity. The silica binder may be commercially available, for example, under the tradename of LUDOX AS-40. However, a sodium form (for example, tradename, LUDOX HS-40) may result in reduced catalytic activity. In order to restrain functions other than the intended function of the binder per se, an ammonium form of the silica binder may be advantageous. In this regard, an ammonium form of the silica binder may contain sodium at a content of, for example, less than about 1% by weight, and less than particularly about 0.1% by weight.

With reference to FIG. 1, a silica powder for support material is provided to prepare a molded support while a silica binder-containing, aqueous dispersion can be prepared.

As can be seen, the silica binder-containing aqueous dispersion may comprise a silica binder alone or in combination with a lubricant (optional ingredient). The lubricant may be typically a hydrolysable polymer. The lubricant increases adhesion between the silica powder for support material and the silica binder in a subsequent step, such as a kneading process, to facilitate the formation of a paste.

According to an exemplary embodiment, the lubricant may be polyvinyl alcohol, polyacrylate, polyvinyl pyrrolidone, cellulose, cellulose ether (e.g., hydroxyethylcellulose, methyl acellulose, etc.), starch, polyamino acids, polytetrahydrofuran, polyethylene glycol, and polyethylene glycol copolymers. They may be used alone or in combination.

According to an exemplary embodiment, a lubricant may be added to an aqueous medium (particularly water) to form a lubricant emulsion. Then, a silica binder is added to the lubricant emulsion to prepare a silica binder-containing emulsion. In order to be uniformly dispersed, the silica binder may be added in an aqueous dispersion form to the lubricant emulsion. The content of the lubricant in the silica binder-containing lubricant emulsion may be, for example, about 0.1 to 20% by weight and particularly about 0.5 to 10% by weight, but is not limited thereto.

According to an alternative embodiment, a silica binder-containing aqueous dispersion can be prepared by adding a silica binder to water instead of the lubricant emulsion and can be used to prepare a molding paste.

According to an exemplary embodiment, a content of the silica binder in the silica binder-containing emulsion or the silica binder-containing aqueous dispersion can be adjusted in light of the range from the minimum to the maximum ratio relative to the silica for support material, in which the silica binder can act as a crosslinker, for example, within about 10 to 60% by weight and particularly within about 20 to 40% by weight.

According to the depicted embodiment, colloidal silica may be used as the silica binder as described above. In consideration of supporting (or impregnating) cobalt through electrostatic adsorption after formation of the molded support, it is advantageous that the colloidal silica may not contain additional cations and anions.

Referring to FIG. 1, after being obtained, a silica binder-containing emulsion or aqueous dispersion is combined with a silica powder for support material to prepare a silica-based molding paste. According to an exemplary embodiment, the silica powder for support material may have a size of, for example, about 30 μm or less, particularly about 20 μm or less, and more particularly about 15 μm or less. However, the numerical ranges should be understood to be illustrative. In order to provide a powder form of the silica for support material, a pulverizing step such as grinding may be performed.

According to an exemplary embodiment, the mixing ratio (weight) of silica binder:silica powder for support material may be, for example, 1:about 0.1 to 10, particularly 1:about 0.5 to 6, and more particularly 1:about 0.6 to 4. Having influence on the cobalt loading amount of the molding support per se and the thermal stability of cobalt, the mixing ratio may be preferably adjusted within the aforementioned range. The molding paste may be prepared using a means known in the art, for example, a kneader.

Then, the molding paste may be used to prepare a silica-based, molded support. The molding method is not limited to particular methods, but any catalyst molding method known in the art, for example, extrusion, pelletizing, or the like may be applied. The paste formation and molding may be conducted in respective separate steps. Alternatively, the paste formation and molding may be conducted simultaneously in a molding process.

In a particular embodiment, the molding support may be obtained by extrusion. As used herein, the term "extrusion" refers to a process used to form an object having a predetermined shape typically by pushing a material (or paste) through a die or an orifice. The silica-based molded product may be prepared to have various shapes (e.g., cylinder, granule, pellet, tablet, sphere, trilobe, etc.) and sizes (or dimensions).

The molded product obtained in the molding process may undergo a drying step, as needed. The drying step may be conducted at, for example, about 15 to 70° C. (particularly about 20 to 50° C., and more particularly room temperature) for about 1 to 24 hours (particularly about 2 to 12 hours). In addition, the molded product may undergo subsequent thermal treatment. The thermal treatment may be conducted in an oxygen-containing atmosphere (e.g., pure oxygen atmosphere or air). The temperature of the thermal treatment may be adjusted within, for example, about 100 to 800° C., particularly within about 150 to 700° C., and more particularly within 500 to 650° C. In addition, the thermal treatment may be conducted for, for example, about 1 to 24 hours, particularly about 1.5 to 12 hours, and more particularly about 2 to 5 hours. In this regard, the thermal treatment may be performed in multiple stages. The thermal treatment may be conducted primarily at a relatively low temperature (e.g., about 100 to 300° C. and particularly about 120 to 200° C.) and secondarily at a relatively high temperature (e.g., about 400 to 800° C. and particularly about 500 to 700° C.). The aforementioned drying and thermal treatment conditions should be understood to be illustrative.

Preparation of First Cobalt- and Alkali Metal-Containing Silica-Based Molded Catalyst According to an embodiment, the silica-based, molded support prepared above is primarily brought about into contact with an alkali metal to form an alkali metal-treated, silica-based, molded support.

Particularly, treatment with an alkali metal may be conducted by adding the silica-based, molded support to an aqueous medium and dissolving an alkali metal salt in the medium. The aqueous medium may be water and particularly distilled water. The silica-based, molded support may be added in an amount of, for example, about 1 to 30% by weight, particularly about 3 to 20% by weight, and more particularly about 5 to 10% by weight, based on the weight of the aqueous medium.

The alkali metal salt may be at least one selected from a hydroxide, a nitrate, a chloride, a carbonate, and a sulfate of the alkali metal, but is not limited thereto. More particularly, alkali metal hydroxide and/or nitrate may be used because these salts are advantageous in pH control without causing the coprecipitation of a cobalt precursor.

In an exemplary embodiment, the alkali metal may be dissolved in an amount of about 0.001 to 3% by weight, particularly about 0.005 to 1% by weight, and more particularly about 0.01 to 0.8% by weight, based on the weight of the silica-based, molded support in the aqueous medium.

In an exemplary embodiment, a pH of the aqueous medium may be adjusted by adding a base before or after the silica-based, molded support comes into contact with the alkali metal salt in the aqueous medium.

By adding a base, the aqueous medium may be adjusted to have a pH of, for example, at least about 9, particularly at least about 9.5, and more particularly about 10 to 12. The reason for increasing the pH of the aqueous medium containing the molded support upon treatment with the alkali metal is to deprotonate the surface of the silica-based molded support. Particularly, the surface may be negatively charged by removing hydrogen ions ($H^+$) from the silanol groups (Si—OH) present thereon. That is, at the point of zero charge (PZC) of the silica molded support, ions are not adsorbed, but silanol groups (hydroxyl groups) are maintained. Thus, the surface of the silica-based molded support is negatively charged by deprotonation through pH adjustment.

As a result, the alkali metal ions can be fixed (or immobilized) or grafted in a form of single-atom to the silica by electrostatic interaction (that is, by electrostatic adsorption) with the silanol anions (SiO⁻) on the deprotonated silica-based molded support surface. In addition, a siloxane, particularly a 3-membered siloxane that coexists with silanol on the silica-based molded support surface forms three silanol anions in the alkaline aqueous medium, which are considered to provide sites to which cobalt can be fixed or immobilized in a form of in a subsequent step.

According to an exemplary embodiment, the base (i.e., alkaline ingredient) may be at least one selected from, for example, sodium hydroxide, potassium hydroxide, ammonium hydroxide, cesium hydroxide, and lithium hydroxide and may be particularly an ammonium-containing base and more particularly ammonium hydroxide (ammonia water). Advantageously, the base added should not cause precipitation in the subsequent step in which an aqueous solution of a cobalt precursor is combined or mixed therewith.

With reference to FIG. 1, the alkali metal-treated, silica-based, molded support may come to contact with the pH-adjusted cobalt precursor aqueous solution to form a first cobalt- and alkali metal-containing silica-based, molded support. To this end, an aqueous solution of a cobalt precursor may be prepared and added with a base (an alkaline ingredient) to afford a pH-adjusted cobalt precursor aqueous solution, separately from the preparation step for the alkali metal-treated, silica-based, molded support.

In this regard, the cobalt precursor may include a cobalt (Co(III)) complex ion having an oxidation number of 3+. For example, $Co(NH_3)_6Cl_3$ may be directly used or at least one cobalt compound (precursor) selected from $Co(NO_3)_2$, $CoCl_2$, and $Co(acac)_3$ is treated with ammonia water and filtered to obtain a precursor including a cobalt complex ion. The employment of $Co(NH_3)_6Cl_3$ may be advantageous for easygoing formation of a cobalt single-atom catalyst because it can minimize the preparations steps.

In an exemplary embodiment, the precursor aqueous solution may contain a cobalt precursor at a concentration of, for example, about 0.1 to 20% by weight, particularly about 0.5 to 10% by weight, and more particularly about 1 to 7% by weight.

Moreover, the pH of the cobalt precursor solution can be adjusted with a base (an alkaline ingredient). As described above, the pH adjustment enables the surface of the silica-based molded support to stably retain a deprotonated state (that is, modified to have a negative charge) in the subsequent step of contacting with the alkali metal-treated, silica-based, molded support, whereby the positively charged cobalt ions ($Co^{3+}$) of the precursor can be fixed or attached to the silica surface through electrostatic adsorption. In this regard, the base ingredient added to the cobalt precursor solution may be at least one selected from those used for the preparation of the alkali metal-treated, silica-based, molded support. By way of example, the base ingredients or basic compounds used in the alkaline metal treatment step and the cobalt fixation (supporting) step may be the same or different. Even in this case, the base ingredient that does not cause precipitation when mixed with an aqueous solution of the cobalt precursor is preferable. In addition, the addition of an base ingredient can adjust the pH of the aqueous cobalt precursor solution to, for example, at least about 9, particularly at least about 9.5, and more particularly about 10 to 12.

As such, the pH-adjusted aqueous solution of a Co(III) precursor (e.g., an aqueous solution of a first cobalt precursor) comes to contact with the alkali metal-treated, silica-based, molded support (typically, contained in a pH-adjusted aqueous medium) to form a first cobalt- and alkali metal-containing silica-based, molded support.

The mixing (combination) ratio between the pH-adjusted cobalt precursor aqueous solution and the alkali metal-treated, silica-based, molded support may be determined considering the amount in which the cobalt ions in the aqueous cobalt precursor solution can be fixed in a form of single-atom (particularly single-atom of a single layer) on the surface of the alkali metal-treated support. In this regard, cobalt ions can be supported in an amount of maximum about 2 to 3% by weight onto the surface of a silica-based support. However, all of the cobalt precursor used cannot be fixed onto the surface of the silica-based support in practice. Thus, an excess of a cobalt (Co(III)) precursor larger than the theoretical amount may be dissolved.

In an exemplary embodiment, the amount of the cobalt precursor may be controlled in a range of from about 1 to 100% by weight, based on the weight of the silica molded support, particularly from about 5 to 50% by weight, and more particularly from about 10 to 30% by weight. In addition, the weight ratio of cobalt:alkali metal in the mixing process may fall within a range of, for example, about 1000:1 to 1:1, particularly about 800:1 to 10:1, more particularly about 600:1 to 50:1, and most particularly 500:1 to 100:1.

After the above-mentioned processes, at least a part of the cobalt ions can be electrostatistically adsorbed onto the surface of the alkali metal ion-adsorbed, silica molded support. Moreover, the alkali metal ions (e.g., K⁺ ions) and the cobalt ions ($Co^{3+}$ ions) can be independently fixed or immobilized in single-atom form on the molded support. Specifically, cobalt having an oxidation number of 3+ (or $Co^{3+}$) as a precursor can strongly bind only to the support surface sites at which 3-membered siloxane rings exist, due to the alkali metal ions already introduced to the silica-based, molded support by the alkali treatment while deposition of cobalt is prevented at the other sites. In other words, the pre-treatment of the silica-based, molded support with the alkali metal restrains the sites available for cobalt deposition.

In contrast, when cobalt is supported without treatment with an alkali metal, cobalt ions are weakly attached to an undesired surface site of the silica-based molded support, for example, a site at which isolated silanol groups exist. The cobalt thus unstably supported undergoes polygomerization (dimerization) with other cobalt during subsequent dehydrogenation reactions and aggregates, inducing a phenomenon of particle formation and acting as a factor to lower the catalytic activity.

According to an exemplary embodiment, the aqueous cobalt precursor solution and the alkali metal-treated, silica-based, molded support (typically, contained in an aqueous medium) may be mixed while stirring. The stirring may be conducted at a speed of, for example, about 200 to 500 rpm, and particularly about 250 to 400 rpm and may be continued, for example, for at least about 3 minutes, particularly about 5 to 40 minutes, and more particularly about 10 to 30 minutes, without limitations thereto. A temperature for the mixing may be set to be, for example, about 10 to 40° C., particularly about 20 to 30° C., and more particularly room temperature, without limitations thereto.

Then, a step of removing as much alkali metal and cobalt remaining unfixed in a single-atom form onto the surface of the first cobalt- and alkali metal-containing silica-based, molded support from the mixed aqueous medium as possible may be conducted as a post-treatment process. This process, which makes the method of the present disclosure different from a conventional impregnation method, is to leave only the alkali metal (or alkaline ions) and cobalt (or $Co^{3+}$) that are fixed in single-atom forms onto the silica surface by electrical interaction while eliminating the others. As in a conventional impregnation method, for example, a cobalt precursor attached in a bulk state on a silica surface induces reduction, aggregation, etc., that lower catalytic activity, during the dehydrogenation.

In full consideration of the foregoing, the first cobalt- and alkali metal-containing silica-based, molded support can be rapidly separated from the liquid (e.g., by settling, filtration, etc.) and as necessary, the separated molded support may be subjected to repeated cycles of adding water, particularly distilled water, stirring, and separating according to an exemplary embodiment. In addition, the separated, molded support may be washed with water, particularly distilled water at least once, particularly two or more times to remove as much the alkali metal and cobalt precursor remain unattached as possible. Next, the first cobalt- and alkali metal-containing (fixed or immobilized) molded support thus obtained may be dried at a temperature of, for example, about 50 to 200° C. and particularly about 70 to 150° C. for, for example, about 3 to 24 hours and particularly about 6 to 12, without limitations thereto. At this time, the cobalt ions still retain an oxidation number of +3.

Returning to FIG. 1, the first cobalt- and alkali metal-containing (fixed or immobilized) silica-based, molded support can be converted to a catalyst by thermal treatment as a subsequent step. The thermal treatment may be conducted in an oxygen-containing atmosphere at, for example, about 250 to 700° C., particularly about 200 to 600° C., and more particularly about 300 to 550° C. So long as it is sufficient to allow the cobalt to change in oxidation number from 3+ to 2+, any thermal treatment time may be taken. For example, the thermal treatment may be continued for about 2 to 24 hours, particularly about 2.5 to 12 hours, and more particularly about 3 to 6 hours.

In the present embodiment, when the alkali metal- and cobalt-adsorbed (fixed or immobilized) silica is thermally treated, the cobalt adsorbed onto the silica changes in oxidation number from 3+ to 2+. However, a part of the cobalt may be reduced from the oxidation number of 3+ to 2+ in the optional drying step conducted prior to the thermal treatment, and then most of the cobalt is reduced to the oxidation number of 2+. Without being bound by a particular theory, the reason why the cobalt retains an oxidation number of 2+ after thermal treatment is explained as follows.

For cobalt with an oxidation number of 3+, only the octahedral structure is possible because six electrons occupy the outmost orbital to enable the formation of six bonds. When the cobalt is reduced to 2+, seven electrons exist in the outmost orbital, thus mainly forming a tetrahedral structure, while an octahedral structure is also possible as in CoO. According to the present embodiment, it is supposed that the cobalt is reduced to 2+ to form a tetrahedral structure because it should structurally bind to the 3-membered siloxane group. On the other hand, in order to return back to 3+, the cobalt should form an octahedron in cooperation with its surroundings. At this time, silicon (Si) does not have any structure other than a tetrahedron in nature, which is in discord with the octahedral structure of cobalt, and thus making it difficult to convert the reduced cobalt to the oxidized state 3+. In contrast, the deactivation arises when the linkage (communication) to Si is cleaved to cause Co metal to aggregate alone. Accordingly, it is considered that the formation of an oxide by contact with oxygen could result in $Co_3O_4$ containing cobalt of the oxidation state 3+.

The cobalt with the oxidation number 2+, converted by heating at a predetermined temperature or higher during the thermal treatment step, is not returned back to the oxidation number 3+ even though the thermal treatment is continued in an oxygen-containing (or oxidation) atmosphere (or calcining atmosphere). The reason is because the single-atom cobalt needs to retain a tetrahedral structure. Furthermore, even when the catalyst is applied to the dehydrogenation conducted at a predetermined temperature or higher, the oxidation state remains unchanged, implying that the catalyst according to the present embodiment is resistant to reduction.

Preparation of Second Cobalt- and Alkali Metal-Containing Silica-Based Shaped Catalyst According to the embodiment depicted in FIG. 1, the support of the first cobalt- and alkali metal-containing silica-based, shaped support catalyst prepared above is not advantageous in terms of loading single-atom cobalt thereto and thus is relatively poor in loading capacity, so that the catalyst exhibits a lower catalytic activity, compared to a powder form. In some cases, since the cobalt and the alkali metal (especially, potassium) compete with each other for adsorption, the cobalt might be loaded in a relatively small amount while a large amount of alkali metal might remain, which has negative influence on the dehydrogenation. In light of this circumstance, a secondary cobalt loading step may be conducted, as needed, according to an exemplary embodiment. The loading amount of cobalt may be additionally increased by loading (applying) cobalt in an basic (alkaline) condition to exchange the alkali metal with cobalt while washing off the alkali meal.

The secondary cobalt loading step may be conducted after the thermal treatment (first thermal treatment) step that has been carried out upon the preparation of the first cobalt- and alkali metal-containing silica-based, shaped support catalyst. Alternatively, cobalt may be secondarily loaded with the first thermal treatment step omitted, followed by a thermal treatment.

As can be seen in FIG. 1, a base ingredient is added to an aqueous solution of a cobalt precursor to give a pH-adjusted, cobalt precursor aqueous solution which is then brought into contact with the first cobalt- and alkali metal-containing silica-based, molded support (or catalyst) to deposit the central metal cobalt in an adsorption manner. After the secondary cobalt loading step, the support is separated from the liquid phase, as described above, optionally undergoes a drying step, and then thermally treated (secondary thermal treatment) in a similar manner to the first thermal treatment step.

The secondary cobalt loading step and the secondary thermal treatment step share technical contents with the primary cobalt loading step and the first thermal treatment step, and thus the description thereof is omitted.

Dehydrogenation

According to other embodiment thereof, the present disclosure provides a process of converting a paraffin, particularly light paraffin (more particularly light paraffin of 2 to 5 carbon atoms) to the corresponding olefin by using the aforementioned cobalt-based, shaped single-atom catalyst. Particularly, the light paraffin may contain propane. In this regard, a feedstock may be provided as a gas phase.

When applied even to a feedstock containing a high content of paraffin, the catalyst can achieve better conversion and selectivity. By way of example, the content of paraffin in a feedstock may be, for example, at least about 50% by volume, particularly at least about 70% by volume, more particularly at least about 80% by volume, and higher than about 99% by volume. This makes a difference from the experimental results in which a feedstock containing at most about 20% by volume is subjected to dehydrogenation in the presence of a conventional single-atom catalyst (e.g., Zn catalyst).

In the dehydrogenation according to an exemplary embodiment, the reaction temperature may range, for example, from about 500 to 700° C., particularly from about 550 to 650° C., and more particularly from about 570 to 620° C. In addition, a pressure of, for example, about 0.3 to 2 bar, particularly about 0.4 to 1.5 bar, and more particularly about 0.5 to 1 bar may be set for the dehydrogenation. As for the gas hourly space velocity (GHSV), its range may be chosen to be, for example, about 100 to 2000 $hr^{-1}$, particularly about 200 to 1500 $hr^{-1}$, and more particularly about 300 to 1000 $hr^{-1}$ in a standard condition. The dehydrogenation conditions may vary depending on kinds of paraffins in the feedstock, active metals in the catalyst, the loading amounts and ratios of alkali metals, etc.

According to an exemplary embodiment, the conversion and selectivity in the dehydrogenation may be, for example, at least about 30% (particularly at least about 40%), and at least about 70% (particularly at least about 80%), respectively.

A better understanding of the present disclosure may be obtained through the following examples which are set forth to illustrate, but are not to be construed as limiting the present disclosure.

EXAFS

In order to investigate the single-atom cobalt in the cobalt single-atom catalyst and to analyze surroundings around the single-atom cobalt, Co K-edge (7.709 keV) X-ray absorption spectroscopy (XAFS) was measured and recorded at the 8C beamline (nano-XAFS (X-ray absorption spectroscopy), 4-20 keV, $10^{12}$ photons/sec) of the Pohang Light Source (PAL PLS-II). The gas was controlled to set the absorption rates of $I_0$ and It+Ir at 15% and 85%, respectively. The monochromator was detuned to 70%. All the specimens except for a reference (0.1 mm) were each powdered, loaded to a 2 mm slit, and made planar before measurement in a transmission mode.

Calculation of Conversion and Selectivity

Conversion and selectivity of propane were calculated according to Equations 1 and 2, below.

$$\text{Conversion Rate of Propane} = \frac{\text{Weight of propane in reactant} - \text{Weight of unconverted propane in product}}{\text{Weight of propane in reactant}} \times 100 \quad \text{[Equation 1]}$$

$$\text{Selectivity for propylene (\%)} = \frac{\text{Weight of propylene in product}}{\text{Weight of propane in reacant} - \text{Weight of unconverted propane in product}} \times 100 \quad \text{[Equation 2]}$$

Preparation Example 1

Preparation of Silica-Based Molded (Extruded) Support

As a silica binder, LUDOX AS-40 (Sigma-Aldrich) weighing 17.2 g was mixed with 3.6 g of distilled water while stirring at 500 rpm to prepare a silica binder solution (dispersion). Separately, silica for support material was ground to fine powder 30 μm or less in size, using a mortar grinder. The finely ground silica powder weighed 10.28 g. The silica binder solution was dropwise added to the ground silica powder to give a silica-silica binder paste. This paste was fed to an extruder and extruded into noodle forms with a constant thickness (size: 1.5 mm). The extrudates thus obtained were sufficiently dried at room temperature and introduced into a heating furnace at which thermal treatment was conducted at 150° C. for 2 hours and then at 600° C. for 2 hours in an air atmosphere to afford a molded silica support.

Preparation Example 2

Preparation of Silica-Based, Shaped (Extruded) Single-Atom Catalyst Having Alkali Metal-Cobalt Loaded Thereto (One-Step Cobalt Loading)

First, 10 g of the silica-based support prepared according to Preparation Example 1 was dispersed in 100 ml of distilled water to which 0.072 g of KOH (Samchun Chemicals) was then added. After being stirred for 30 minutes, the dispersion was controlled to have a pH of 11 by adding 28 wt % conc. ammonia water (Samchun Chemicals) thereto. In a separate beaker, 2.5 g of a cobalt precursor ($Co(NH_3)_6Cl_3$; TCI) was dissolved in 50 ml of distilled water. The aqueous cobalt precursor solution was controlled to have a pH of 11 by adding 28 wt % conc. ammonia water (Samchun Chemicals) thereto.

Next, the aqueous cobalt precursor solution was immediately added to the dispersion containing the silica molded support and the alkali metal, followed by stirring at room temperature for 10 minutes. The stirred sample was left for 5 minutes and the supernatant thus formed was decanted. The residue was added with 200 ml of distilled water and then stirred again for 10 minutes. The stirred sample was left and the supernatant thus formed was decanted. The residue was filtered in a vacuum and washed several times with distilled water. Thereafter, the washed filtrate was dried at room temperature and then additionally at 125° C. The dried sample was heated to 300° C. at a rate of 5° C./min and thermally treated for 3 hours at the temperature to prepare a cobalt-loaded single-atom catalyst having cobalt and alkali metal loaded thereto.

Preparation Example 3

Preparation of Silica-Based, Molded (Extruded) Single-Atom Catalyst Having Alkali Metal-Cobalt Loaded Thereto (Two-Step Cobalt Loading)

First, 10 g of the silica-based support prepared according to Preparation Example 1 was dispersed in 100 ml of distilled water to which 0.072 g of KOH (Samchun Chemicals) was then added. After being stirred for 30 minutes, the dispersion was controlled to have a pH of 11 by adding 28 wt % conc. ammonia water (Samchun Chemicals) thereto. In a separate beaker, 2.5 g of a cobalt precursor ($Co(NH_3)_6Cl_3$;

TCI) was dissolved in 50 ml of distilled water. The aqueous cobalt precursor solution was controlled to have a pH of 11 by adding 28 wt % conc. ammonia water (Samchun Chemicals) thereto.

Next, the aqueous cobalt precursor solution was immediately added to the dispersion containing the silica molded support and the alkali metal, followed by stirring at room temperature for 10 minutes. The stirred sample was left for 5 minutes and the supernatant thus formed was decanted. The residue was added with 200 ml of distilled water and then stirred again for 10 minutes. The stirred sample was left and the supernatant thus formed was decanted. The residue was filtered in a vacuum and washed several times with distilled water. Thereafter, the washed filtrate was dried at room temperature and then additionally at 125° C. The dried sample was heated to 300° C. at a rate of 5° C./min and thermally treated for 3 hours at the temperature to prepare a primary cobalt-loaded single-atom catalyst having cobalt and alkali metal loaded thereto.

To additionally load cobalt to the primary cobalt-loaded single-atom catalyst, first, 10 g of the primary cobalt-loaded single-atom catalyst was dispersed in 100 ml of distilled water. The dispersion was controlled to have a pH of 11 by adding 28 wt % conc. ammonia water (Samchun Chemicals) thereto. In a separate beaker, 2.5 g of a cobalt precursor ($Co(NH_3)_6Cl_3$; TCI) was dissolved in 50 ml of distilled water. The aqueous cobalt precursor solution was controlled to have a pH of 11 by adding 28 wt % conc. ammonia water (Samchun Chemicals) thereto.

Thereafter, the aqueous cobalt precursor solution was immediately added to the solution (dispersion) of the primary cobalt-loaded single-atom catalyst, followed by stirring at room temperature for 10 minutes. The stirred sample was left for 5 minutes and the supernatant thus formed was decanted. The residue was added with 200 ml of distilled water and then stirred again for 10 minutes. The stirred sample was left and the supernatant thus formed was decanted. The residue was filtered in a vacuum and washed several times with distilled water.

The washed filtrate was dried at room temperature and then additionally at 125° C. The dried sample was heated to 300° C. at a rate of 5° C./min and thermally treated for 3 hours at the temperature to prepare a molded cobalt single-atom catalyst.

Comparative Preparation Example 1

Preparation of Cobalt-Loaded Single-Atom Catalyst by Using Commercial Silica Support in an Extrudate Form A cobalt-loaded single-atom catalyst was prepared in the same manner as in Preparation Example 2, with the exception that 20 g of the commercially available silica (SP100, Evonik), which is processed into an extrudate form, was used as the silica-based, molded support.

Comparative Preparation Example 2

Preparation of Cobalt Single-Atom Catalyst Molded from Mixture of Powder-Type Cobalt Single-Atom Catalyst and Silica Binder First, 20 g of commercially available silica was dispersed in 200 ml of distilled water in which 0.144 g of KOH was then dissolved. The dispersion was controlled to have a pH of 11 by adding 28 wt % conc. ammonia water (Samchun Chemicals) thereto.

In a separate beaker, 5 g of a cobalt precursor ($Co(NH_3)_6Cl_3$; TCI) was dissolved in 50 ml of distilled water. The aqueous cobalt precursor solution was controlled to have a pH of 11 by adding 28 wt % conc. ammonia water (Samchun Chemicals) thereto.

Next, the aqueous cobalt precursor solution was immediately added to the dispersion containing the silica and the alkali metal, followed by stirring at room temperature for 10 minutes. The stirred sample was left for 5 minutes and the supernatant thus formed was decanted. The residue was added with 200 ml of distilled water and then stirred again for 10 minutes. The stirred sample was left and the supernatant thus formed was decanted. The residue was filtered in a vacuum and washed several times with distilled water. Thereafter, the washed filtrate was dried at room temperature and then additionally at 125° C. The dried sample was heated to 300° C. at a rate of 5° C./min and thermally treated for 3 hours at the temperature to prepare a cobalt-loaded single-atom catalyst.

A mixture of the prepared catalyst and a silica binder was molded into a cobalt single-atom catalyst. To this end, first, 0.52 g of the lubricant PVA (Sigma-Aldrich, polyvinylalcohol) was mixed with 2.0 g of distilled water and the mixture was stirred while 8.58 g of the silica binder LUDOX AS-40 was dropwise added.

The cobalt-loaded single-atom catalyst prepared above was ground to a size of 30 μm or less. To 5.18 g of the catalyst powder thus obtained, a mixture of the lubricant and the silica binder was dropwise added, while stirring. Before being dried, the resulting paste was introduced to an extruder and extruded into noodle forms with a constant thickness (size: 1.5 mm). The extrudates thus obtained were sufficiently dried at room temperature and introduced into a heating furnace at which thermal treatment was conducted at 150° C. for 2 hours and then at 600° C. for 2 hours in an air atmosphere to afford a shaped cobalt single-atom catalyst.

Comparative Preparation Example 3

Preparation of Cobalt Single-Atom Catalyst Molded from Mixture of Powder-Type Cobalt Single-Atom Catalyst and Alumina Binder First, 20 g of commercially available silica was dispersed in 200 ml of distilled water in which 0.144 g of KOH was then dissolved, followed by stirring for 30 min. The dispersion was controlled to have a pH of 11 by adding 28 wt % conc. ammonia water (Samchun Chemicals) thereto.

In a separate beaker, 5 g of a cobalt precursor ($Co(NH_3)_6Cl_3$; TCI) was dissolved in 50 ml of distilled water. The aqueous cobalt precursor solution was controlled to have a pH of 11 by adding 28 wt % conc. ammonia water (Samchun Chemicals) thereto.

Next, the aqueous cobalt precursor solution was immediately added to the dispersion containing the silica and the alkali metal, followed by stirring at room temperature for 10 minutes. The stirred sample was left for 5 minutes and the supernatant thus formed was decanted. The residue was added with 200 ml of distilled water and then stirred again for 10 minutes. The stirred sample was left and the supernatant thus formed was decanted. The residue was filtered in a vacuum and washed several times with distilled water. Thereafter, the washed filtrate was dried at room temperature and then additionally at 125° C. The dried sample was heated to 300° C. at a rate of 5° C./min and thermally treated for 3 hours at the temperature to prepare a cobalt-loaded single-atom catalyst.

The cobalt-loaded single-atom catalyst prepared above was ground to a size of 30 μm or less. 12.5 g of the catalyst powder thus obtained was added together with 12.5 g of the alumina binder boehmite (SASOL) to a PP container and mixed for 12 hours in a roll mixer.

Separately, 60% nitric acid (Sigma-Aldrich) was weighed to an amount corresponding to 0.25 g of pure nitric acid and diluted in distilled water to give a 10 cc aqueous nitric acid solution. This nitric acid solution was dropwise added to the cobalt single-atom catalyst powder-boehmite mixture and well mixed to give a paste of the mix powder. The cobalt single-atom catalyst powder-boehmite-nitric acid mixed paste was well kneaded and then extruded into noodles with a constant thickness (size: 1.5 mm) in an extruder. The extrudates thus obtained were sufficiently dried at room temperature and introduced into a heating furnace at which thermal treatment was conducted at 150° C. for 2 hours and then at 600° C. for 2 hours in an air atmosphere to afford a shaped cobalt single-atom catalyst.

Comparative Preparation Example 4

Preparation of Powder-Type Cobalt Single-Atom Catalyst

First, 20 g of commercially available silica was dispersed in 200 ml of distilled water in which 0.144 g of KOH was then dissolved, followed by stirring for 30 min. The dispersion was controlled to have a pH of 11 by adding 28 wt % conc. ammonia water (Samchun Chemicals) thereto.

In a separate beaker, 5 g of a cobalt precursor ($Co(NH_3)_6Cl_3$; TCI) was dissolved in 50 ml of distilled water. The aqueous cobalt precursor solution was controlled to have a pH of 11 by adding 28 wt % conc. ammonia water (Samchun Chemicals) thereto.

Next, the aqueous cobalt precursor solution was immediately added to the dispersion containing the silica and the alkali metal, followed by stirring at room temperature for 10 minutes. The stirred sample was left for 5 minutes and the supernatant thus formed was decanted. The residue was added with 200 ml of distilled water and then stirred again for 10 minutes. The stirred sample was left and the supernatant thus formed was decanted. The residue was filtered in a vacuum and washed several times with distilled water. Thereafter, the washed filtrate was dried at room temperature and then additionally at 125° C. The dried sample was heated to 300° C. at a rate of 5° C./min and thermally treated for 3 hours at the temperature to prepare a cobalt-loaded single-atom catalyst.

EXAFS Analysis

Figure 2:
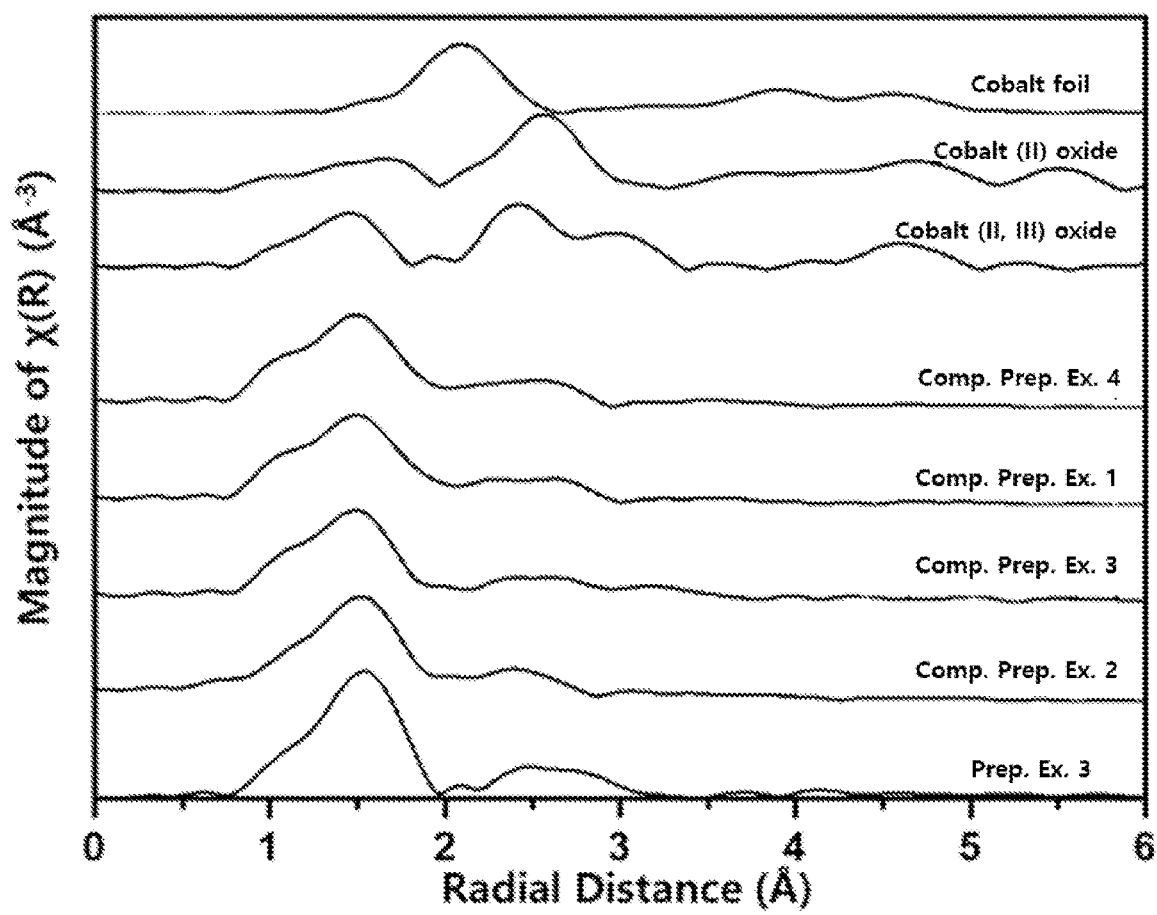
FIG. 2 is a view showing EXAFS spectra for cobalt single-atom catalysts and molded cobalt single-atom catalysts prepared in Preparation Example 2 and Comparative Preparation Example 2 to 5.

The cobalt single-atom catalysts and shaped cobalt single-atom catalysts prepared in Preparation Example 3 and Comparative Examples 1 to 4 were analyzed for EXAFS and the spectra are given in FIG. 2.

As can be seen in the figure, Co foil strongly peaked at around 2.1 Å, which is characteristic of the Co—Co bond of cobalt metal. For the Co oxides $Co_3O_4$ and CoO, two peaks were observed: first peak for Co-0 (1.5 to 1.7 Å) and second peak for Co—Co (2.5 to 3 Å). In the particles, the oxides form crystals where unit cell structures are repeated, accounting for the development of the second peak.

Meanwhile, the cobalt single-atom catalyst powder (Comparative Preparation Example 4) and shaped catalysts (Preparation Example 3 and Comparative Preparation Examples 1 to 3) all showed well developed first peaks, but second peaks were remarkably attenuated, indicating that Co atoms are away from each other, with no bonds formed therebetween. In view of the Si—O bond which supports Co, the weak peaks are considered to come from the Co—Si bond.

The analysis results above imply that the shaped catalysts prepared exist in single-atom forms.

Analysis of Catalyst Composition

Compositions of cobalt and potassium in the catalysts prepared in Preparation Example 2 and Comparative Preparation Examples 1 to 5 were analyzed using ICP-AES and are summarized in Table 2, below.

TABLE 2

| Catalyst | Co Content (wt %) | K Content (ppm) |
|---|---|---|
| Comparative Preparation Example 4 (powder-type cobalt single-atom catalyst) | 2.86 | 60.1 |
| Comparative Preparation Example 1 (cobalt-loaded single-atom catalyst using extrudate-type commercial silica support) | 1.13 | 33 |
| Comparative Preparation Example 2 (catalyst molded from mixture of powder-type cobalt single-atom catalyst and silica binder) | 2.22 | 102 |
| Comparative Preparation Example 3 (catalyst molded from mixture of poweder-type cobalt single-atom catalyst and alumina binder) | 1.88 | 44 |
| Preparation Example 2 (silica-based molded (extruded) single-atom catalyst having alkali metal-cobalt loaded thereto: one-step cobalt loading) | 1.02 | 612 |
| Preparation Example 3 (silica-based, molded (extruded) single-atom catalyst having alkali metal-cobalt loaded thereto: two-step cobalt loading) | 2.06 | 193 |

Comparison was made between the single-atom cobalt-loaded catalysts (Preparation Example 2 and 3) using the silica molded supports prepared according to Preparation Examples and the catalysts prepared in Comparative Preparation Examples. As is understood from the data of Table 2, the catalyst prepared in Preparation Example 2 exhibited a cobalt load which amounted to 36% of that in the conventional powder-type catalyst advantageous for cobalt single-atom loading and which was similar to that of the catalyst having cobalt loaded to a commercially available extruded silica. However, the catalyst of Preparation Example 2 still retained a spare space to which cobalt could be loaded when the potassium amounts were compared. In addition, the cobalt load in the catalyst prepared according to Preparation Example 3 was similar to that of the catalyst molded from a mixture of 70% of the powder-type catalyst and a binder. The three catalysts were all understood to have cobalt occupying most of the sites available for cobalt (that is, cobalt and potassium are loaded to similar sites and as a result, the amount of potassium was notably reduced).

From the foregoing features, catalysts having similar contents of cobalt loaded thereto were compared and observed. In addition, comparison was made between Preparation Examples 2 and 3 in which cobalt were loaded in one-step and two-step manners, respectively. The potassium that still occupied active sites to which cobalt was not yet loaded in the first step was substituted by cobalt in the second step, so that the active sites capable of performing dehydrogenation were increased.

Experimental Example 1

In this experimental example, a reactant gas containing high contents of paraffins was subjected to dehydrogenation in the presence of the cobalt-loaded single-atom catalysts prepared in Preparation Example 3 and Comparative Preparation Examples 2 to 4 to synthesize olefins.

The dehydrogenation for catalyst evaluation was carried out using a ¾-inch quartz tube reactor (¾ inches for diameter in the catalyst loading region and ¼ inch for diameter for the other tube region). Flow rates of the gas were controlled using a mass flow controller and the product gas from the reactor was analyzed using an online gas chromatography apparatus (50 m HP-PLOT column).

The shaped catalysts were pulverized to L/D and D/d ratios suitable for being arranged within the reactor. Only particles with 16 to 40 mesh sizes were selected. Of them, 6 cc (about 3 g) was weighed and supported by quartz wool in the reaction tube through which $N_2$ (99.999%, Daesung Industrial Gases Co. Ltd.) was then allowed to flow at a flow rate of 100 cc/min while the temperature was elevated from room temperature to 590° C. at a speed of 5° C./min. Subsequently, the condition was maintained for 1 hour for stabilization during which a micro air pump installed at the rear of the reactor was used to reduce the pressure in the reaction tube to about 0.5 bar.

For dehydrogenating paraffin, the reactant gas containing 99.5% propane (regas) was introduced at a flow rate of 20 cc/min into the reactor. The composition of the gas from the reactor was analyzed using FID (flame ionization detector). The results are shown in FIG. 3.

Figure 3:
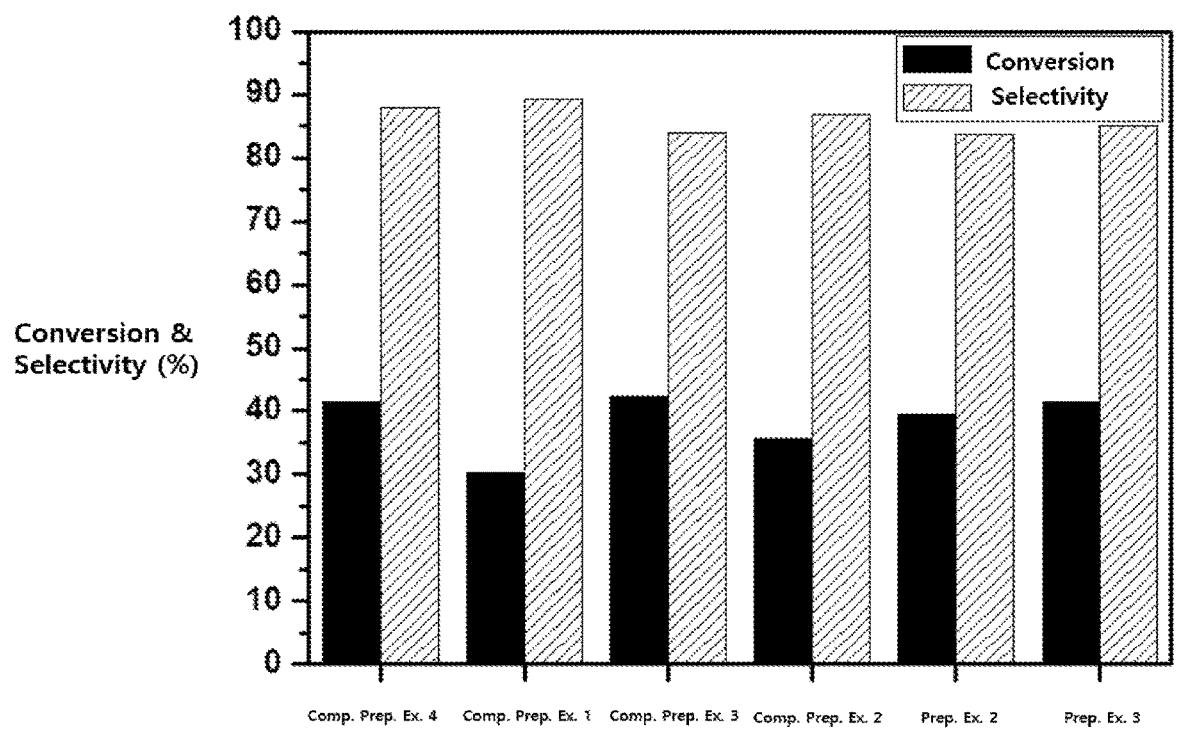
FIG. 3 is a graph showing results of propane dehydrogenation using molded cobalt single-atom catalysts and powder-type cobalt single-atom catalysts.

Referring to FIG. 3, the catalyst having cobalt loaded to commercially available extruded silica showed low activity for dehydrogenation as expected from the relatively low cobalt load whereas the catalyst prepared in Preparation Example 2 was of high dehydrogenation activity in spite of a low cobalt load. In addition, the catalyst prepared in Preparation Example 3 (increased cobalt load level) was observed to perform dehydrogenation at the same level as the powder-type catalyst.

In contrast, the two shaped catalysts prepared in the Comparative Preparation Examples were low in conversion (Comparative Preparation Example 2; molded with silica binder) or in selectivity (Comparative Preparation Example 3; molded with alumina binder) even though having cobalt loads similar to that in the catalyst prepared in Preparation Example 3.

As described hitherto, even when exposed to a high temperature (e.g., about 500° C. or higher) during dehydrogenation of paraffins, particularly light paraffins to corresponding to olefins, the single-atom catalyst using a silica-based, molded support according to an embodiment of the present disclosure is effectively prevented from undergoing the aggregation or sintering of the cobalt by the action of the alkali metal fixed in a single-atom form to the surface of the silica-based, molded support, thereby retaining catalytic activity for a long period of time.

Furthermore, even in the case of employing a molded support, which is suitable for commercialization, the catalyst according to an embodiment of the present disclosure enables the central metal cobalt to maintain a single-atom form and thus can guarantee dehydrogenation activity equivalent to those of powder-type catalysts.

Particularly, when dehydrogenation is conducted in the presence thereof, the catalyst according to an embodiment of the present disclosure can achieve notable conversion for feedstocks containing a high content of paraffins and excellent selectivity for olefins.

Accordingly, it should be understood that simple modifications and variations of the present disclosure may be easily used by those skilled in the art, and such modifications or variations may fall within the scope of the present disclosure.

What is claimed is:

1. A method for preparation of a cobalt-based, shaped single-atom catalyst, the method comprising the steps of:
    combining a silica binder and a silica powder for support material in an aqueous medium to prepare a molding paste;
    molding the paste into a silica-based, molded support;
    contacting the silica-based, molded support with an alkali metal salt in an aqueous medium to form an alkali metal-treated, silica-based, molded support, before or after which pH adjustment is made with a base, wherein at least a part of the alkali metal ions are electrostatically adsorbed on the surface of the silica-based, molded support;
    contacting the alkali metal-treated, silica-based, molded support with an aqueous solution of a cobalt precursor to form a cobalt- and alkali metal-containing, silica-based, molded support, the aqueous solution of the cobalt precursor being adjusted in pH by adding a base thereto, with the cobalt precursor having an oxidation number of 3+, wherein at least a part of the cobalt ions having an oxidation number of 3+ is electrostatically adsorbed on the alkali metal-treated, silica-based, molded support; and
    thermally treating the cobalt- and alkali metal-containing silica-based, molded support such that cobalt having an oxidation number of 2+ and alkali metal having an oxidation number of 1+, respectively, exist in an isolated form of single-atom on the silica-based, molded support,
    wherein the cobalt having an oxidation number of 2+ is tetrahedrally coordinated at a three-membered siloxane ring present on the surface of the silica-based, molded support.

2. A method for preparation of a cobalt-based, shaped single-atom catalyst, the method comprising the steps of:
    combining a silica binder and a silica powder for support material in an aqueous medium to prepare a molding paste;
    molding the paste into a silica-based, molded support;
    contacting the silica-based, molded support with an alkali metal salt in an aqueous medium to form an alkali metal-treated, silica-based, molded support, before or after which pH adjustment is made with a base, wherein at least a part of the alkali metal ions are electrostatically adsorbed on the surface of the silica-based, molded support;
    contacting the alkali metal-treated, silica-based, molded support with an aqueous solution of a cobalt precursor to form a cobalt- and alkali metal-containing, silica-based, molded support, the aqueous solution of the cobalt precursor being adjusted in pH by adding a base thereto, with the cobalt precursor having an oxidation number of 3+, wherein at least a part of the cobalt ions having an oxidation number of 3+ is electrostatically adsorbed on the alkali metal-treated, silica-based, molded support;
    contacting the cobalt- and alkali metal-containing, silica-based, molded support with an aqueous solution of a second cobalt precursor to form a second cobalt- and alkali metal-containing, silica-based, molded support, the aqueous solution of the second cobalt precursor being adjusted in pH by adding a base thereto, with the second cobalt precursor having an oxidation number of 3+ to form a second cobalt- and alkali-metal-containing silica-based molded support; and thermally treating the second cobalt- and alkali metal-containing silica-based, molded support such that cobalt having an oxidation number of 2+ and alkali metal having an oxidation number of 1+, respectively, exist in an isolated form of single-atom on the silica-based, molded support, wherein the cobalt having an oxidation number of 2+ is tetrahedrally coordinated at a three-membered siloxane ring present on the surface of the silica-based, molded support.

3. The method of claim 2, further comprising a step of thermally treating the cobalt- and alkali metal-containing silica-based, molded support, prior to the step of forming the second cobalt- and alkali metal-containing silica-based, molded support.

4. The method of claim 1, wherein the silica powder for support material is amorphous silica.

5. The method of claim 4, wherein the amorphous silica comprises wet (hydrated) silica.

6. The method of claim 1, wherein the silica binder is colloidal silica.

7. The method of claim 1, wherein a weight ratio of the silica binder to the silica powder for support material ranges from 1:0.1 to 1:10.

8. The method of claim 1, wherein the step of preparing a molding paste comprises:

preparing (i) a silica binder-containing lubricant emulsion or (ii) a silica binder-containing aqueous dispersion; and combining the silica binder-containing lubricant emulsion or the silica binder-containing aqueous dispersion with the silica powder for support material, wherein the silica binder-containing lubricant emulsion or the silica binder-containing aqueous dispersion contains the silica binder at a content of 10 to 60% by weight.

9. The method of claim 8, wherein the silica binder-containing lubricant emulsion contains the lubricant at a content of 0.1 to 20% by weight.

10. The method of claim 1, wherein the silica-based, molded support has at least one shape selected from the group consisting of a cylinder, a granule, a pellet, a tablet, a sphere, and a trilobe.

11. The method of claim 1, wherein alkali metal is at least one selected from the group consisting of sodium (Na), potassium (K), and cesium (Cs), and the alkali metal salt is at least one selected from a hydroxide, a nitrate, a chloride, a carbonate, and a sulfate of the alkali metal.

12. The method of claim 1, wherein the step of forming an alkali metal-treated, silica-based, molded support employs the silica-based, molded support in an amount of 1 to 30% by weight, based on the weight of the aqueous medium, and the alkali metal salt in an amount of 0.001 to 3% by weight, based on the weight of the silica-based, molded support in the aqueous medium.

13. The method of claim 1, wherein the base in the step of forming an alkali metal-treated, silica-based, molded support is an ammonium-containing base and is used to adjust the pH to at least 9.

14. The method of claim 1, wherein the cobalt precursor in the aqueous solution is a precursor comprising a complex ion of cobalt having an oxidation number of 3+(Co (III)), and is contained at a concentration of 0.1 to 20% by weight.

15. The method of claim 1, wherein the cobalt precursor in the step of forming the cobalt- and alkali metal-containing silica-based, molded support is used in an amount of 1 to 100% by weight, based on the weight of the silica molded support.

16. The method of claim 1, wherein the thermal treatment is carried out at a temperature of 250 to 700° C. in an oxygen-containing atmosphere.

17. The method of claim 1, wherein the cobalt-based, shaped single-atom catalyst contains cobalt and alkali metal at a content of 0.5 to 3% by weight and 0.00001 to 1% by weight, respectively, with the weight ratio of cobalt(Co)/alkali metal ranging from 1 to 1000.

* * * * *